United States Patent [19]

Whang

[11] Patent Number: 5,306,511
[45] Date of Patent: Apr. 26, 1994

[54] ALKALINE ADDITIVE FOR DRINKING WATER

[75] Inventor: Sang Y. Whang, Miami, Fla.

[73] Assignee: Sang Whang Enterprises, Inc., Miami, Fla.

[21] Appl. No.: 33,011

[22] Filed: Mar. 18, 1993

[51] Int. Cl.$^5$ ................................................ A23L 2/00
[52] U.S. Cl. ......................................... 426/66; 426/74
[58] Field of Search ..................... 426/66, 74; 514/378

[56] References Cited

U.S. PATENT DOCUMENTS 3,821,392  6/1974  Harned ................................. 514/378
4,693,832  9/1987  Hurst ..................................... 426/66

*Primary Examiner*—George Yeung

[57] ABSTRACT

A highly concentrated alkaline solution is formed by combining potassium hydroxide (KOH) with sodium hydroxide (NaOH) so that an alkaline drinking water may be formulated. One part of concentrated alkaline additive solution is diluted with several parts of distilled water in a one ounce mixture. The additive is further characterized by combining potassium hydroxide with sodium hydroxide in a range of about 95% potassium hydroxide and 5% sodium hydroxide to about 50% potassium hydroxide to about 50% sodium hydroxide. One ounce bottles of 75% potassium hydroxide to about 25% sodium hydroxide (dilute with distilled water) are supplied with a droplet cap in order to conveniently add the additive into ordinary glass of drinking water in order to readily form an alkaline drinking water.

15 Claims, No Drawings

ALKALINE ADDITIVE FOR DRINKING WATER

FIELD OF THE INVENTION

The field of the present invention relates broadly to methods and solutions pertaining to health. More specifically, the invention pertains to a source of alkaline drinking water that is prepared by use of a convenient, readily dispensable concentrated additive solution that is added to normal drinking water.

Still more particularly, the invention relates to an additive of a concentrated alkaline solution formed by a combination of potassium hydroxide (KOH) and sodium hydroxide (NaOH) amounts selected within a specific range. The additive solution is added to ordinary drinking water in order to increase the pH of the water to a range of about 9 to 12.

DESCRIPTION OF PRIOR ART

New medical developments and devices are emerging on the domestic market at an increasing pace. In Germany a Skin resistance Measurement (SRM) device is being used not only to diagnose a patient without taking any blood samples, but also the SRM device finds use in testing whether a person's reflexes agree or disagree with a particular sample being tested. This SRM device is a significant aid in diagnosing and treating patients.

Another device in a closely related field is an electrically powered water ionizer machine[1]. Originally developed over thirty years ago in Japan, water ionizers have been successfully introduced in the United States within the last decade or so. The chief purpose of these ionizer machines is to prepare alkaline drinking water from regular bottled or tap water. Accordingly, a ready demand for alkaline drinking water, recognized as being beneficial for some individuals, has developed in the health field.

For a more detailed description of these devices and acidic and alkaline water, please see a book written by inventor entitled, *Reverse Aging*. copyright 1990 and published by JSP Publishing. P.O. Box 570987, Perrine Fla. 33257-0987.

Water ionizer machines do not add any minerals to, for example, regular tap water that is put into the machine. Instead, the ionizer has positive and negative electrodes that split the alkaline minerals in the tap water to one side for use and the water's acidic minerals to another side for discard. The pH in the final drinking water output from the machine, depending upon the mineral content of the water supplied to it, is an alkaline drinking water of increased oxygen that has a pH in the range of about 8.5 to about 10.5. Ionized water from such machines is essentially acid free because the ionization process removes the acid minerals from the machine's drinking water output. The acid water from such machines is discarded or finds use by florists for preserving cut flower shelf life.

Such water ionizers, although commercially successful, do suffer from several limitations. For example, these ionizer machines are expensive, ranging in price from about $600.00 to $1,000 each. In addition, such machines are relatively bulky, and thus are inconvenient for use by travelers. In addition, the convenience is somewhat in question since it does require a ready source of water and electricity.

In spite of their shortcomings, however, the aforementioned machines have clearly established a recognized need for alkaline water. An increasing segment of the consuming public are now beginning to relay on a readily available supply of ionizer-produced alkaline water. What was not solved by such machines, however, was a simple, effective power-free way to convert ordinary tap or bottled water into the alkaline water that is experiencing an increased consumer demand.

This invention overcomes the deficiencies of the ionizer machines, and provides a simple, ready-to-use concentrated additive that may easily be added to bottled or tap water in order to convert same into an alkaline water having a pH in the range of about 9.5 to 10.5. In use, a few drops of the highly concentrated alkaline booster solution of this invention, is added to a glass or regular drinking water in order to change the water into alkaline water of the desired pH.

SUMMARY OF THE INVENTION

This invention provides a highly concentrated alkaline solution that is formed by combining potassium hydroxide (KOH) with sodium hydroxide (NaOH). More particularly, the invention combines one part of concentrated alkaline additive solution diluted with nine parts of distilled water packaged in one ounce mixtures. The diluted additive mixture is commercialized and sold by the assignee of this invention under the tradename of AlkaLife TM.

The additive of this invention is further characterized by a diluted mixture of about one part additive to nine parts distilled water wherein the additive itself is formed by combining potassium hydroxide with sodium hydroxide in a range of about 95% potassium hydroxide and 5% sodium hydroxide to about 50% potassium hydroxide and about 50% sodium hydroxide. In one of my preferred embodiments, one ounce bottles of 75% potassium hydroxide to about 25% sodium hydroxide, in the one to nine ratio—is combined with distilled water.

Packaged one ounce bottles are supplied with a droplet cap in order to allow the user to conveniently measure the additive into an ordinary glass of drinking water. The amount of distilled wall diluent may, of course, vary since the purpose of the distilled water is simply to dilute the more concentrated hydroxide solution into a more manageable droplet form for addition to a glass of drinking water. Thus, if diluted by the ratio of one part concentrate to nineteen parts distilled water, one must add twice as many drops to achieve the same pH value of alkaline drinking water.

OBJECTS OF THE INVENTION

It is an object of the present invention to provide a more convenient source of alkaline drinking water.

It is another object of my invention to prepare alkaline drinking water by use of an additive rather than relying upon a relatively more complicated and expensive water ionizer machine.

It is still another object of this invention to formulate an alkaline drinking water by use of an additive prepared from distilled water in combination with selected amounts of potassium hydroxide and sodium hydroxide.

It is yet another object of this invention to increase a lower-valued pH alkaline water made by an ionizer to a higher pH value by use of a small amount of alkaline additive to the ionizer water.

It is still a further object of this invention to provide a readily-available substitute for ionizer machine-produced alkaline drinking water.

DESCRIPTION OF PREFERRED EXAMPLE EMBODIMENT AND BEST MODE OF THE INVENTION

Turning now to a detailed description of the invention, which may be understood without reference to any drawing, one must first understand that many minerals are present in ordinary drinking water. Such tap water naturally has a pH of about 7 or 8, and in its natural form, is not alkaline—although some alkaline minerals may be present.

The purpose of this invention is to supply an additive solution to purposely turn the low pH of ordinary drinking water into alkaline drinking water. Moreover, the invention will yield an alkaline drinking water having a pH of about 10 to 10.5. The alkaline water of this invention is not a medicine to treat or cure any disease. It does, however, neutralize excess body acids and helps the body dispose of such body acids. By so doing, the health of many people have improved in a natural way which is enhanced by alkaline drinking water formulated in accordance with the booster additive of this invention.

The predominant alkaline minerals found in ordinary drinking water are calcium and magnesium, not potassium or sodium. There is no known natural supply of drinking water where the predominant alkaline mineral is potassium. Therefore, the predominant alkaline minerals in high pH alkaline water, without employing the booster additive of this invention, are generally considered to be calcium and magnesium. The invention, in contrast, is an alkaline water made by adding potassium hydroxide and sodium hydroxide to regular water.

A summary of the development of the invention is believed to be helpful to understanding the basis for the preferred embodiment of my alkaline booster additive. Sodium hydroxide is commonly used to increase the alkalinity of any liquid. However, sodium (Na) is reportedly harmful to ones health and thus sodium free diets have ben advocated. Calcium (Ca) and magnesium (Mg) hydroxide concentrations are very murky and do not dissolve easily in water. For these reasons these alternatives were not deemed acceptable in a search for a convenient alkaline concentrate.

In the human body, it is important to maintain a proper balance of potassium and sodium. A prolonged use of potassium hydroxide alone may cause an imbalance of potassium and sodium. For this reason, a combination of potassium hydroxide and sodium hydroxide was tried next in my research and development program. A significant issue was finding the right percentage combination of the number of sodium and potassium atoms in the solution.

The average amount of sodium and potassium minerals in a 154 pound adult man is 63 grams and 150 grams, respectively. Since the atomic weights of sodium and potassium are 23 and 39 respectively, the ratio of the number of atoms to the average normal body amounts of these minerals, is 63/23 for sodium and 150/39 for potassium. These ratios translate into 41.6% sodium atoms to 58.4% potassium atoms. However, in today's average diet, unless one is conscientiously avoiding sodium, there are more foods that contain sodium than potassium. Accordingly, the amount of sodium should be reduced somewhat.

At this point in my research, I made the decision to test the effectiveness of the amounts of sodium and potassium in the additive with an SRM (Skin Resistance Measurement) device. My test was conducted by testing the reactions of several different people's cells to the alkaline water. The first phase of the test was to see if the alkaline water with a pH value of 10 was beneficial to people in the test group. The test results indicate that this high pH alkaline water was beneficial to everyone tested except for two people who were life time vegetarians suffering from an over alkaline syndrome. For them, the alkaline water tested as being harmful.

A second phase of the test was to see if the addition of the booster exclusively made of potassium hydroxide made a difference. For those persons in the group for whom the alkaline water was helpful, the addition of the booster gave even better results on the SRM device. During this phase of the test, irradiated strawberries were tested in conjunction with the water and the booster. The SRM meter was set to a reading of 100 without any strawberries, alkaline water or booster. When irradiated strawberries were tested, the meter reading went down to 40, indicating that it was harmful. Adding alkaline water prepared by an ionizer machine increased the SRM reading to 60. Adding the potassium hydroxide (KOH) booster of the invention caused the reading to go up to 80.

The third phase of the test was to try out different percentage combinations of sodium hydroxide and potassium hydroxide. Using a limited number of different combination samples, the following general results were obtained. The optimum percentage combination of sodium to potassium hydroxide seems to vary depending upon the individual. I found that a common range was between 30 and 35% sodium and 70 and 65% potassium.

It seems that the reading on a SRM device is a function of how much sodium one has within his body. For a person who watches their sodium intake very carefully, the optimum percentage of sodium in the additive was as high as 50%. I estimate that the individual range may start as low as 20% sodium to as high as 50% sodium depending upon the natural sodium content of the individual. One thing that was noted is that the booster solutions of the invention improved the SRM readings whether 20% or 50% sodium content was present in the booster additive. What I am focussing on in the preferred embodiment is that percentage which on balance will give the best result for each particular individual.

With irradiated strawberries, the optimum combinations changed with the same individual. In general, the sodium content got lower for the optimum result, i.e., the most common range was between 20 and 25% sodium hydroxide. As a matter of fact, the combination of alkaline water and the booster of 20 to 25% sodium hydroxide and 80 to 75% potassium hydroxide caused all the ill effects of the irradiated strawberries to disappear, at least as far as the SRM reading was concerned.

Since we, the consumers, do not know for sure which foods are being irradiated or not, I decided on a 25% sodium hydroxide and 75% potassium hydroxide combination as the standard booster mixture.

In the future when SRM measurement instruments become more readily available, optimum individualized boosters may be tailor-made as individualized additive combinations. Such boosters, however, should nevertheless be formulated from sodium and potassium hydroxide in accordance with the principles of this invention. My estimate is that the optimum range for an individual should range from 5% sodium (95% potassium) to 50% sodium (50% potassium). Until such individualized SRM information is available on a widespread basis, however, a 25% (sodium) to 75% (potassium) combination will be used as a standard booster additive for creating alkaline drinking water.

It should also be understood, of course, that one could also add a small amount of other alkaline minerals such as calcium and/or magnesium to the additive booster solution of this invention. However, the ratio of sodium to potassium should still be maintained within the general range of 5 to 50%.

A one oz. bottle of the booster additive of my invention contains about 600 to 800 drops. When two drops of this booster is added to a 10 oz. glass of regular tap water, the water pH value increases from approximately 7 or 8 to about 10 to 10.5. This pH change represents approximately 50 mgs of potassium and 9.8 mgs of sodium per glass of water. The daily requirement of sodium and potassium is about 3,000 mgs and 1,000 mgs, respectively.

The purpose of this booster is to make a drinking water whose pH value is approximately 10 to 10.5. This is a typical pH value of the water produced by the water ionizer when there are high amounts of alkaline minerals in the tap water. High pH alkaline water from an ionizer has little or no acid minerals since the ionizer removes them. High pH alkaline water produced by the booster has all the acid minerals that were in the originally supplied water. If the booster were added to the alkaline water from an ionizer, it will further boost the alkalinity of that water and the water, of course, does not have acid minerals.

In some geographical area, tap water contains very small amounts of alkaline minerals. In such cases, the pH value of the water produced by the ionizer is low, even under 9. The alkaline booster helps that situation. Thus, the booster additive of this invention is also useful as a supplement for alkaline water from an ionizer machine.

While my invention has been described with reference to a particular example of preferred embodiments, it is my intention to cover all modifications and equivalents within the scope of the following appended claims. It is therefore requested that the following claims be given a liberal interpretation which is within the spirit and scope of my contribution to this art.

What is claimed is:

1. A concentrated alkaline booster solution that is to be added to normal drinking water in order to increase the pH value of said drinking water, said booster solution comprising:
   a combination of potassium hydroxide and sodium hydroxide mixed in a ratio of about one part combination to about nine parts water in order to formulate said concentrated alkaline booster.

2. An alkaline booster solution of claim 1 wherein the combination of potassium hydroxide and sodium hydroxide is in a range from 95% potassium hydroxide and 5% sodium hydroxide to 50% potassium and 50% sodium hydroxide.

3. An alkaline booster solution of claim 1 wherein the combination of potassium hydroxide and sodium hydroxide is in a range consisting of from 80% potassium hydroxide and 20% sodium hydroxide, to about 70% potassium hydroxide and 30% sodium hydroxide.

4. Alkaline drinking water having a predominant alkaline mineral, said drinking water comprising:
   a value for the pH of the drinking water being within a range of about 9 to 12; and further wherein the predominant alkaline mineral in said drinking water which contributes to the water's alkalinity is supplied by a liquid additive which is a formulated by a combination of potassium hydroxide, sodium hydroxide and water.

5. The alkaline drinking water of claim 4 wherein the combination of potassium hydroxide and sodium hydroxide in said liquid additive is in a range consisting of from 95% potassium and 5% sodium hydroxide to 50% potassium and 50% sodium hydroxide.

6. The alkaline drinking water of claim 4 wherein said liquid additive is formulated by a combination of potassium hydroxide and sodium hydroxide in a range consisting of from 80% potassium and 20% sodium hydroxide to 70% potassium and 30% sodium hydroxide.

7. The alkaline drinking water of claim 4 wherein said drinking water is ordinary tap water and said water is made into alkaline drinking water by the addition thereto of said potassium hydroxide and sodium hydroxide liquid additive solution.

8. The alkaline drinking water of claim 4 wherein said drinking water is near alkaline water produced from ordinary tap water that has been processed by an ionizer machine, and the pH of said ionizer machine water is raised by said liquid additive to a pH value of about 9 to 12.

9. The alkaline drinking water of claim 4 wherein said additive is a liquid solution formed by diluting about nine parts of distilled water with one part of said potassium hydroxide and sodium hydroxide mixture.

10. A method of formulating an alkaline drinking water, comprising the steps of:
    adjusting a pH value for the drinking water to about 8 to 12;
    supplying said pH value by mixing a predominant alkaline mineral in said drinking water in the form of an additive which is a formulated by
    combining potassium hydroxide and sodium hydroxide mixed together and added to distilled water.

11. The method of claim 10 wherein the combining step is further characterized by:
    selecting the amounts of said potassium hydroxide and sodium hydroxide in said additive to fall within a range consisting of from 95% potassium hydroxide and 5% sodium hydroxide to 50% potassium hydroxide and 50% sodium hydroxide.

12. The method of claim 10 wherein the combining step is further characterized by:
    selecting the amounts of said potassium hydroxide and said sodium hydroxide to fall within a range consisting of from about 80% potassium hydroxide and 20% sodium hydroxide to about 70% potassium hydroxide and 30% sodium hydroxide.

13. The method of claim 10 and further characterized by the steps of:
    drawing an amount of ordinary tap water;
    converting said ordinary tap water into alkaline drinking water having said pH value by adding thereto a small quantity of said potassium hydroxide and sodium hydroxide additive solution.

14. The alkaline drinking water of claim 10 wherein said drinking water is alkaline water produced free of acidic minerals from ordinary tap water that has been processed by an ionizer machine, and said method further includes the steps of:
    raising the pH of said water to a pH amount of about 9 to 12, by mixing therewith a small quantity of said additive.

15. The alkaline drinking water of claim 14 wherein said additive solution is formed by:
    diluting about nine parts of distilled water with one part of a liquid mixture formed from said potassium hydroxide and sodium hydroxide solution.

* * * * *